United States Patent [19]

Norelli

[11] Patent Number: 4,820,277

[45] Date of Patent: Apr. 11, 1989

[54] SAFETY COVER FOR SYRINGE NEEDLES

[76] Inventor: Robert A. Norelli, 1010 Road 9, Powell, Wyo. 82435

[21] Appl. No.: 156,544

[22] Filed: Feb. 16, 1988

[51] Int. Cl.$^4$ .............................................. A61M 5/32
[52] U.S. Cl. ..................................... 604/192; 604/263
[58] Field of Search ................ 604/192, 198, 263, 187

[56] References Cited

U.S. PATENT DOCUMENTS 4,664,259  5/1987  Landis ........................... 604/192 X
4,747,836  5/1988  Luther ................................ 604/198

Primary Examiner—John D. Yasko
Attorney, Agent, or Firm—Zarley, McKee, Thomte, Voorhees & Sease

[57] ABSTRACT

A syringe needle safety cover includes a pair of jaw members pivotally mounted in diametric sides of a syringe barrel to move between a closed position, wherein the jaws are longitudinally abutting, and an open position. A groove in each jaw cooperates to form a tubular aperture between the jaws into which the needle is encased. In one embodiment, the jaws are attached to a barrel of a syringe. In a second embodiment, the jaws are attached to an adapter which fits between a conventional syringe and a conventional needle. In a third embodiment, the jaws are attached to the base of a needle, and may be connected to any conventional syringe. The jaws are provided with locking clips which lock the jaws together around the needle. Another embodiment of the invention provides a fluid-tight safety cover by the insertion of a split gasket-type seal, one portion of the gasket being attached to each jaw. The gasket material is compressible, such that it will surround a portion of the needle and seal fluids into the tubular aperture. A mechanical actuator may be provided for any one of the embodiments of the invention, and includes a pair of lever arms which are connected at one end to each jaw and at the other end to an actuator bar. The actuator bar is thumb-actuated, and moves along the syringe barrel, causing the jaws to open, or close, depending upon the direction of movement of the actuator bar.

8 Claims, 6 Drawing Sheets

SAFETY COVER FOR SYRINGE NEEDLES

TECHNICAL FIELD

The present invention generally relates to syringes, and relates more particularly to protective devices for covering a needle on a syringe.

BACKGROUND OF THE INVENTION

There is an increased public awareness of the spread of infectious disease by contact with contaminated syringe needles. While casual contact with a needle is not typically harmful, accidental sticking with a used needle will dramatically increase the chance of spread of harmful substances from the needle to the bloodstream.

One method presently known for protecting against needle sticks is in the use of a disposable needle cover which encases the "clean" needle upon purchase. This cylindrical case is held in one hand when attaching the needle to a syringe, and then removed while the needle and syringe are used. After the needle is used, the case is held in one hand while the needle is reinserted into the case with the other hand. Because the cylindrical case is relatively small in diameter, it takes some amount of concentration to reinsert the needle into the case without sticking a finger. In the rushed pace typical of modern hospitals, the extra care necessary to prevent injury is not always carried out.

An attempt to avoid this problem can be seen in the redesign of the syringe case, which holds the syringe and covered needle. An opening in one end is used to hold the needle casing, and the syringe case is designed to stand vertically on a flat surface. It is intended that the nurse reinsert the used needle into this freestanding case with only one hand — to avoid sticking the other hand with the needle. However, in practicality, it is unlikely that the time and effort would be taken to attempt to stand the container on a flat surface and then guide the needle into the cylindrical case, without using the other hand as a guide.

Another method for protecting against needle sticks was the redesign of a needle having a short hollow tube which would slide over the needle and snap into place. However, this method also has drawbacks. First, the redesign of the needle produces a needle having an effective length approximately twice that of standard needles. This change of length can substantially effect the way in which the needle and syringe are utilized by a nurse or doctor in administering a shot or taking blood. The extra length requires the user to concentrate on using a substantially different needle length when using the syringe. The extra time necessary to utilize the extra length needle effects both the convenience and the efficiency of using such needles. Another disadvantage of the extra length needle is the greater tendency for the needle tip to become deflected away from the central axis of the needle and syringe, thereby reducing the accuracy required to insert the needle in a vein or the like.

Another drawback of the slidable cover devices is in the method of covering the needle. The tube-shaped cover is located near the base of the needle, and is grasped between the thumb and index finger of one hand and is moved towards the sharp tip of the needle, while the other hand holds the syringe. A sharp force is required in order to snap the tube into its secured position covering the needle tip. If the case is not secured on the first try, the recoil of the fingers can be caught on the tip of the needle causing a needle stick. The device also requires the use of both hands — an inefficient and undesirable requirement.

It is therefore a general object of the present invention to provide an improved safety cover for needles.

Another object is to provide a safety cover for needles which will provide a secure enclosure for a used needle.

Another object is to provide a safety cover for a needle which is capable of single-handed operation.

Yet another object of the present invention is to provide a safety cover for a needle which utilizes a minimum number of moving parts.

A further object is to provide a safety cover for a needle which is simple in operation, inexpensive to manufacture, and aesthetic in appearance.

Still another object is to provide a safety cover for needles which may be manufactured as part of the conventional syringe barrel, part of the removable conventional needle, or on an adapter inserted between the syringe and needle.

Another object is to provide a one-piece nondetachable safety cover for needles which prevents accidental misplacement of the cover.

Yet another object of the present invention is to provide a safety cover for a needle which maintains current syringe/needle dimensions and configuration for universal utility.

A further object is to provide a safety cover which is fluid-tight for use on patients having highly infectious diseases.

Still another object is to provide a safety cover which is operable with a single hand.

Yet a further object of the present invention is to provide a safety cover which is operable by hand motion away from the needle tip.

These and other objects will be apparent to those skilled in the art.

SUMMARY OF THE INVENTION

The safety cover of this invention includes a pair of cooperable, pivoting jaws which are movable between an open position, wherein the jaws are positioned generally parallel and on diametric sides of a syringe barrel, and a closed position wherein the jaws enclose the needle of a syringe. A groove in each jaw cooperate to form a tubular aperture between said jaws in which the needle is encased. In one embodiment, the jaws are attached directly to a barrel of a syringe for use with any conventional needle. In a second embodiment, the jaws are attached to an adapter which fits between a conventional syringe and a conventional needle. In a third embodiment, the jaws are attached to the base of a needle, and may be connected to any conventional syringe.

The jaws are provided with locking clips which lock the jaws together around the needle. A second embodiment of the clips allow the clips to be released, to provide a safety cover for syringe needles that are used more than once.

Another embodiment of the invention provides a fluid-tight safety cover by interposing a split gasket-type seal in the tubular aperture, one portion of the gasket being attached to each jaw. The gasket material is compressible, such that it will surround a portion of the needle and seal fluids into the tubular aperture.

Another version of the fluid-tight safety cover has a rib projecting from the flat surface on one jaw surrounding its groove. A groove on the other jaw cooperates with the rib to form a seal along the periphery of the safety cover.

A mechanical actuator is provided for use with any one of the embodiments of the invention. The actuator includes a pair of lever arms which are connected at one end to each jaw and at the other end to an actuator bar. The actuator bar is thumb-actuated, and moves along the syringe barrel, causing the jaws to open, or close, depending upon the direction of movement of the actuator bar.

DESCRIPTION OF THE PREFERRED EMBODIMENTS

Figure 1:
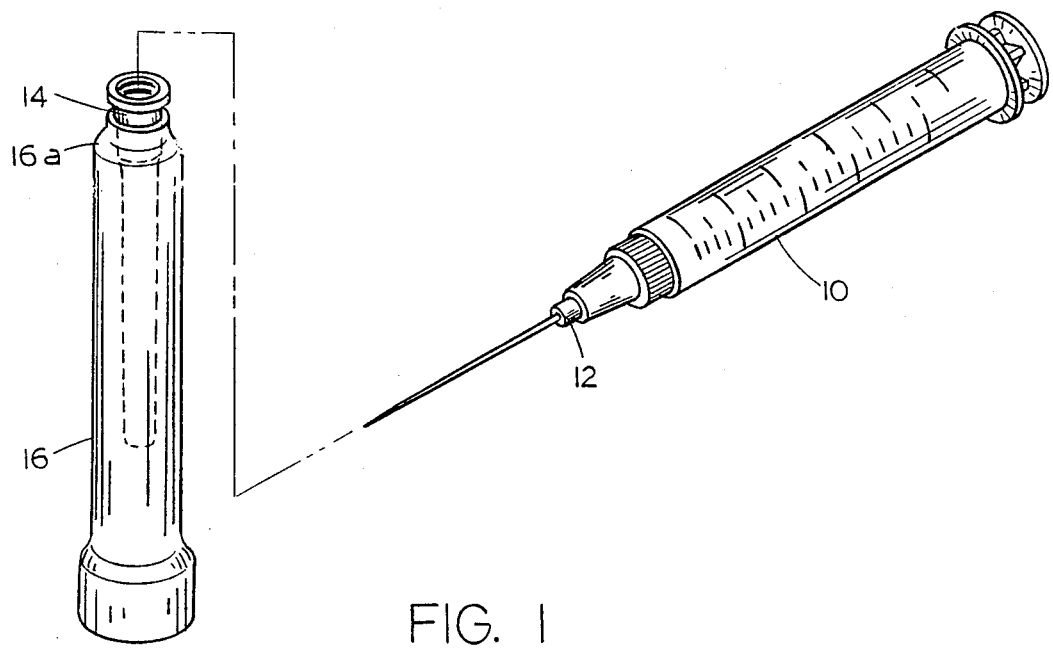
FIG. 1 is a perspective view of a prior art needle, syringe, and a needle case for enclosing a used needle.

Referring now to the drawings, in which identical or corresponding parts are identified by the same reference numeral, and more particularly to FIG. 1, a conventional syringe 10 having a conventional removable needle 12 is shown in a prior art method for safely disposing of a used needle. A generally cylindrical needle case 14 is removable from needle 12, and is part of the original package purchased with the needle 12 and syringe 10. The entire syringe 10, needle 12, and needle case 14 are housed in syringe holder 16, when purchased. As shown in FIG. 1, needle 12 is used by removing needle case 14, the needle case then being inserted into the upper end 16a of syringe holder 16. Syringe holder 16 may then be held in the hand while needle 12 is being reinserted into needle case 14, or stood vertically on a flat surface so that needle 12 may be guided into needle case 14 without using a hand to hold syringe holder 16.

Figure 2:
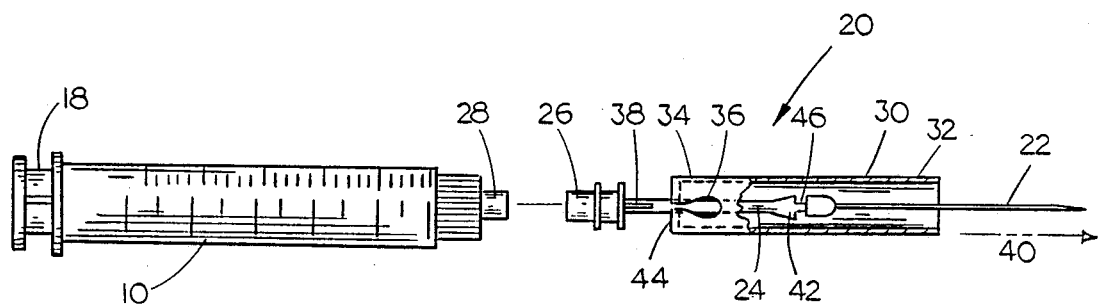
FIG. 2 is an elevational view of a prior art needle having a slidable safety cover thereon.

Referring now to FIG. 2, a conventional syringe 10 having a plunger 18 is shown with another prior art safety device designated generally at 20. Safety device 20 replaces the conventional needle 12 (shown in FIG. 1) with a needle portion 22 and extender shaft 24. Extender shaft 24 has a conventional female connecting portion 26 which is removably connectable to male connecting portion 28 on syringe 10. Thus, safety device 20 may be easily installed and removed from syringe 10, just as conventional needles 12 of other prior art devices.

A slidable hollow tube portion 30 is open at both ends 32 and 34, and is movable between a needle-revealing position and a needle-encasing position. End 34 of hollow tube 30 has a slot 36 cut therein which will grip a rib 38 affixed to shaft 24 so as to retain tube 30 in its needle-revealing position. End 34 grips rib 38 by a biasing action, and may be easily released by sliding tube 30 towards needle 22, as shown by arrow 40.

Elongated shaft 24 includes an enlarged portion 42 which acts to spread a collar portion 44 in end 34 of hollow tube 30. Thus, by applying force in the direction of arrow 40 on hollow tube 30, collar portion 44 may be forced past enlarged portion 42 on shaft 24 to be retained in annular slot 46, with tube 30 secured in the needle-encasing position to protect against needle sticks. However, as described hereinabove, the amount of force required to secure tube 30 in its needle-encasing position can cause accidents if the tube is not secured on the first attempt. It is noted that tube 30 is fully open at end 32, such that in the needle-encasing position, the tube fails to provide protection from contaminated body fluids which may be on the needle.

Figure 3:
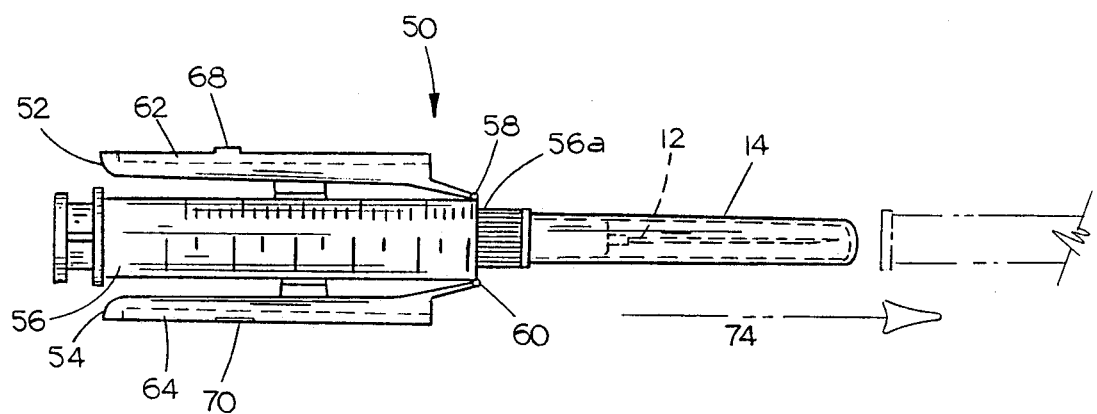
FIG. 3 is a side elevational view of a syringe with the safety cover of the present invention thereon, showing the position of the safety cover during use of the needle.
Figure 4:
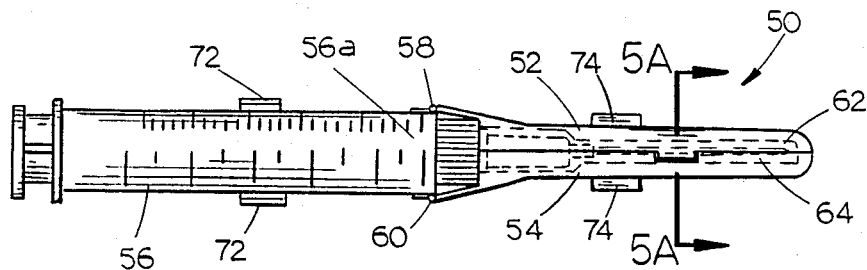
FIG. 4 is an elevational view of a syringe with the safety cover of this invention thereon, the safety cover in a secured, closed condition.
Figure 5:
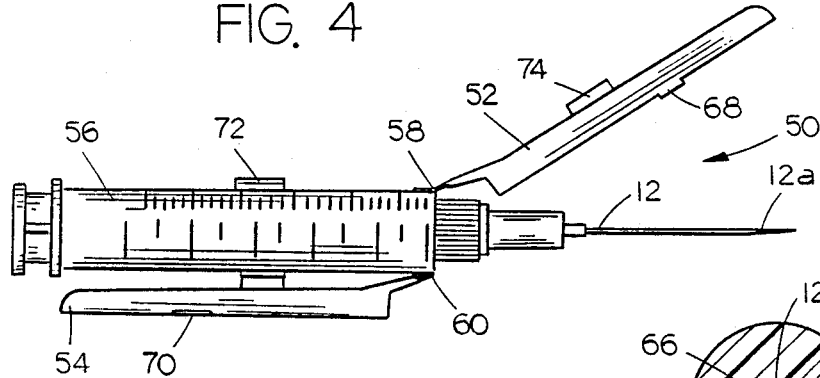
FIG. 5 is an elevational view of a syringe with one jaw of the present invention being moved into a closed position.

Referring now to FIGS. 3-5, the improved safety cover of this invention is designated generally at 50 and includes a pair of elongated, generally semi-cylindrical jaws 52 and 54 which are cooperable to completely encase a conventional needle 12. Each jaw 52 and 54 is connected to a syringe barrel 56 at the needle-adjacent end 56a by a hinge 58 and 60, respectively. It is noted that hinges 58 and 60 are intended to describe the pivotal action of the jaws, rather than a specific structural element. In the preferred embodiment, the inventor contemplates that jaw 52 be comprised of a single piece of flexible, resilient plastic material which is bendable at hinge 58. Similarly, jaw 54 may be a single piece of resilient plastic material which is bendable at hinge 60. The type of plastic used for construction of conventional syringe barrels has been found to be a satisfactory material for jaws 52 and 54. This material allows the jaw to be pivoted about hinge 58 (as shown in FIGS. 3 and 5) into a needle-encasing position (shown in FIG. 4) without breaking at the bend. Of course, hinges 58 and 60 may also be conventional hinge structures utilizing pins and the like.

Figure 5A:
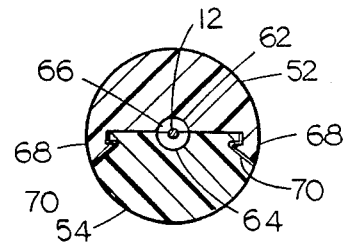
FIG. 5A is an enlarged cross-sectional view taken at lines 5A—5A in FIG. 4.
Figure 6:
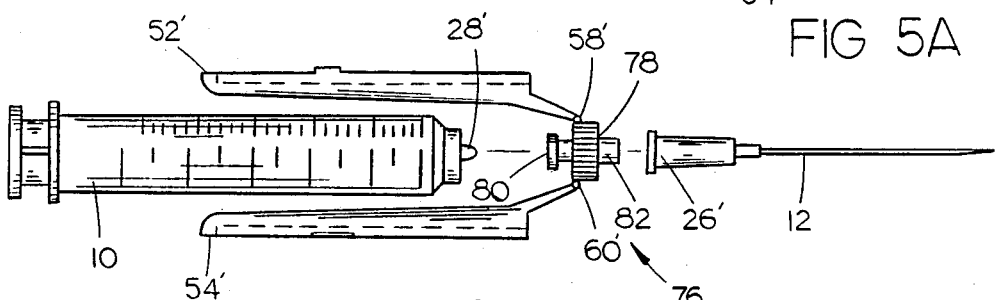
FIG. 6 is a second embodiment of the present invention with the safety cover connected to an adapter between the syringe and needle.

As shown in FIGS. 4 and 5A, each jaw 52 and 54 is a generally solid semi-cylinder having a longitudinal groove 62 and 64 respectively which cooperate to form a tubular aperture 66 which will encase needle 12. A pair of projecting locking clips 68 are diametrically opposed and mounted on jaw 52 to cooperate with receiving sockets 70 in jaw 54, as shown in the drawings. Clips 68 and sockets 70 allow the jaws 52 and 54 to be positively secured together to encase needle 12.

A pair of clips 72 are affixed to the syringe barrel 56 and will cooperate with clips 74 so as to hold jaws 52 and 54 adjacent the syringe barrel (as shown in FIG. 3) until released by the application of pressure on each jaw outwardly and perpendicular to syringe barrel 56. In use, FIG. 3 shows the needle-revealing position in which the safety cover 50 is originally positioned. Needle casing 14 is removed, as shown by arrow 74, to reveal a sterile conventional needle 12. Once the syringe and needle have been used, jaws 52 and 54 are easily released from clips 72 so as to pivot about hinges 58 and 60 (as shown in FIG. 5). Jaws 52 and 54 are then snapped shut (as shown in FIG. 4) around needle 12, and locked in place by clips 68 in sockets 70. It can be seen that at no time is it necessary for the fingers of the user to be near the sharp tip 12a of needle 12 during the encasement of the needle. Even if accidental slipping of the fingers were to occur, the fingers are not in proximity to the sharp needle tip 12a, thereby preventing even a remote possibility of a needle stick. The pivotal motion of the jaws 52 and 54 of safety cover 50 thereby perform a safety function in themselves, in that they require a different, safer motion of the hands in sealing the jaws about the needle 12, than prior art devices.

The mounting of jaws 52 and 54 on the syringe barrel 56, as shown in FIGS. 3–5, allows the incorporation of the safety device 50 on any size syringe for conventional and special purposes. Further, the use of a conventional syringe barrel 56 allows the use of a standard needle on the syringe.

Since there are a vast number of syringe barrels and needles already existing on the market, the inventor has provided a second embodiment of the invention, designated generally at 76, which utilizes a pair of jaws 52' and 54' which are mounted by hinges 58' and 60' to an adapter 78. Adapter 78 has a female connecting socket 80 which is connectable to the conventional male connecting portion 28' of a syringe 56. Adapter 78 also has a male connecting portion 82 disposed axially to female connecting socket 80 which has dimensions for receiving the conventional female connecting socket 26 of a conventional needle 12. Thus, the second embodiment of safety cover 76 may be utilized with any conventional syringe 56 and needle 12 already on the market.

Figure 7:
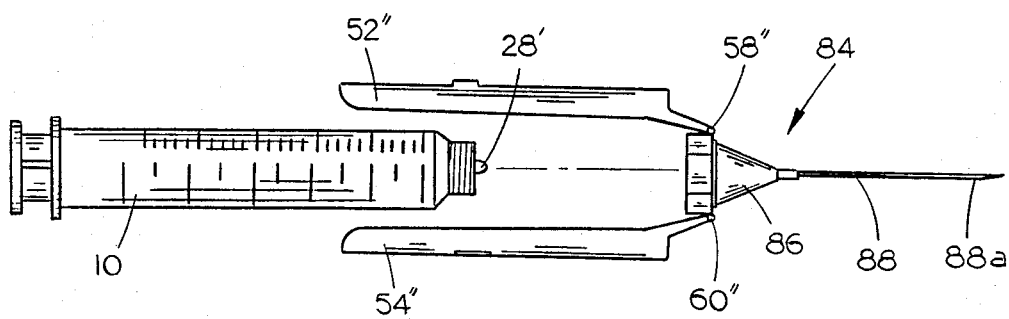
FIG. 7 is an elevational view of a third embodiment of this invention with the hinged safety cover attached to the base of a needle.

Referring now to FIG. 7, a third embodiment of the invention is designated generally at 84 and includes a pair of jaws 52" and 54" attached by hinges 58" and 60" to a base 86 having a needle 88 affixed thereto. Safety cover 84 is thereby designed for use with conventional syringes 10 already on the market. Base portion 86 has a female connecting socket portion 90 which is adapted to be connectable with male connecting portion 28' of syringe 10. It is noted that the overall length from female connecting socket 90 to the tip 88a of needle 88 of this embodiment of safety device 84, is substantially the same as the overall length of a conventional needle 12. This length is important since the skill and efficiency of the nurses and doctors in giving shots and the like rely upon a substantially uniform needle length.

Figure 8:
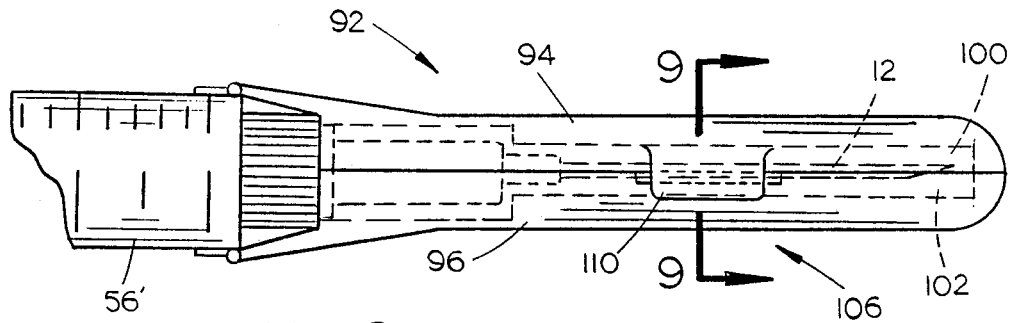
FIG. 8 is an enlarged elevational view of a fourth embodiment of the present invention in a closed position.
Figure 9:
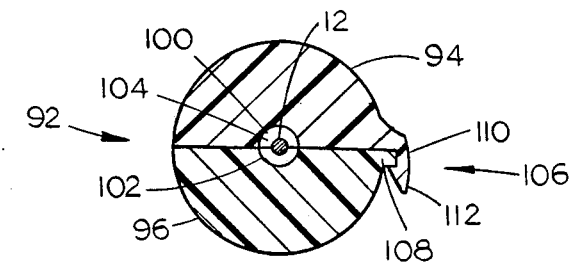
FIG. 9 is a sectional view taken at lines 9—9 in FIG. 8.

Referring now to FIGS. 8 and 9, a fourth embodiment of the safety cover of this invention is designated generally at 92 and is designed with a releasable locking clip for use on syringes that require more than one use. Safety cover 92 includes a pair of generally semi-cylindrical jaw portions 94 and 96 which are cooperable to encase a conventional needle 12 on a syringe 98. As shown in FIG. 9, a groove 100 and a groove 102 are cut along the length of each jaw 94 and 96 respectively to form a tubular aperture 104 which will encase needle 12 when jaws 94 and 96 are secured together. A releasable lock mechanism, designated generally at 106, includes an upstanding, longitudinally-oriented rib 108 which will receive an overlapping resiliently-bendable lip portion 110, as shown in the drawings. Lip portion 110 has a projecting edge 112 which may be lifted to release rib 108 from lip portion 110. The releasable lock mechanism 106 is particularly useful for anesthesiologists, who administer medication at various intervals using the same syringe and needle. Safety cover 92 allows the anesthesiologists to safely carry the syringe and needle between actual usage of the needle.

Figure 10:
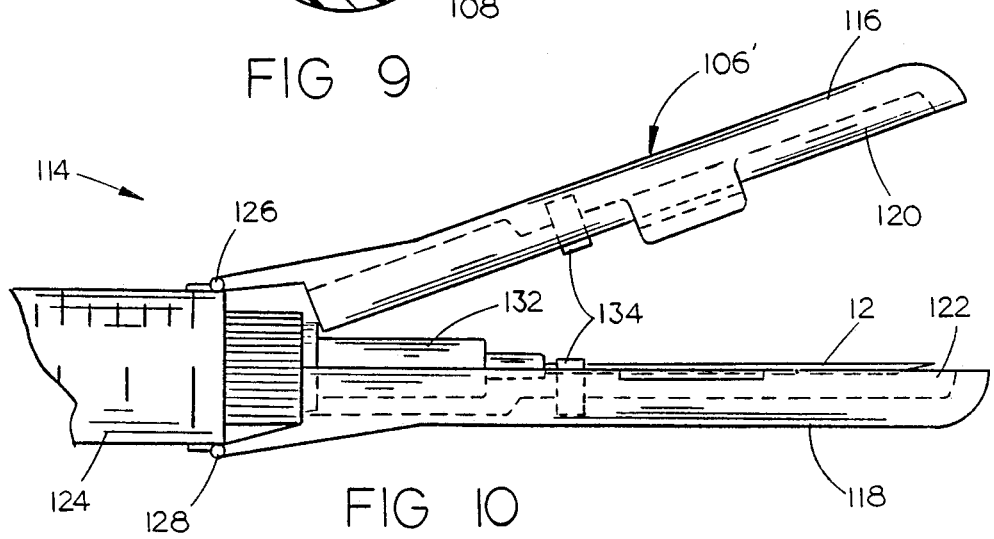
FIG. 10 is an enlarged elevational view of a fifth embodiment of the invention.
Figure 11:
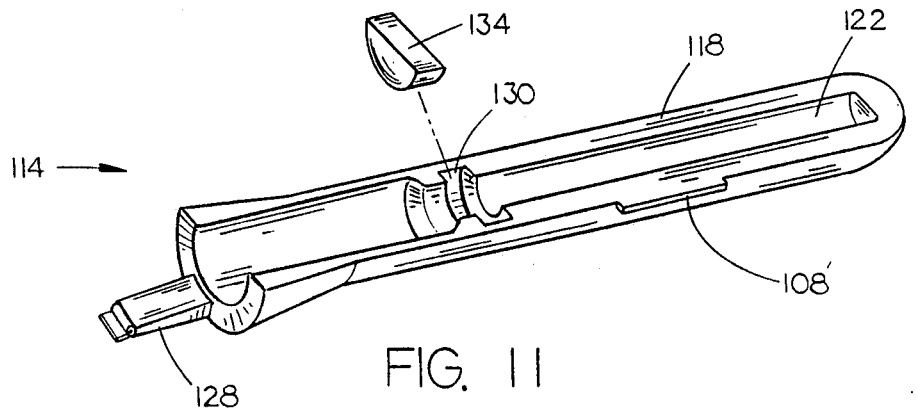
FIG. 11 is a perspective view of one jaw of the embodiment of the invention shown in FIG. 10.

Referring now to FIGS. 10 and 11, a fifth embodiment of the safety cover of this invention is designated generally at 114 and is designed to provide a fluid-tight safety cover. Safety cover 114 includes a pair of generally semi-cylindrical jaws 116 and 118 having a longitudinal groove 120 and 122, respectively, cut therein to encase a conventional needle 12. Each jaw 116 and 118 are connected to a syringe barrel 124 of conventional dimension at hinges 126 and 128, respectively. Hinges 126 and 128 may be a resilient bendable material which is bent to provide a pivotal movement for jaws 116 and 118, in a manner similar to that disclosed in the previous embodiments. A releasable lock mechanism 106' is shown on safety cover 114, and is of the same type as that described with respect to FIGS. 8 and 9.

One half of an annular groove 130 is cut into each jaw 116 and 118 perpendicularly to the longitudinal axis of jaws 116 and 118. Annular groove 130 is located adjacent to the base of needle 12. One half of a disc-shaped, resilient gasket 134 is affixed in each annular groove half 130 in each jaw 116 and 118, such that upon closure of jaws 116 and 118, gasket 134 will form a tight seal between the gasket halves. Gasket 134 is a compressible material which will form a fluid-tight seal around the shaft of the needle when the needle is pressed between the two halves, as shown in FIG. 10. Thus, upon closing jaws 116 and 118 any contaminated fluid on needle 12 will be sealed within the tubular aperture formed by grooves 120 and 122 in safety cover 114.

Figure 12:
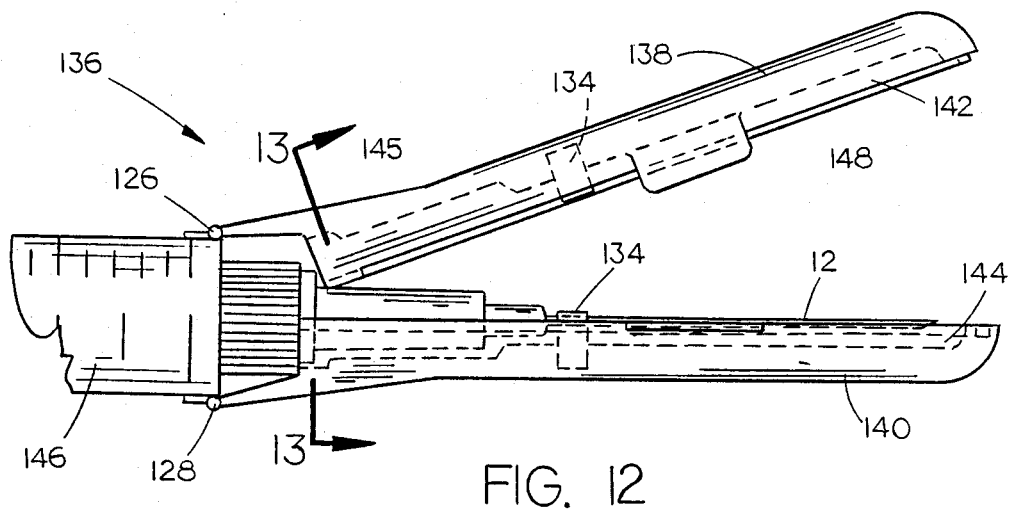
FIG. 12 is an elevational view of sixth embodiment of the present invention.
Figure 13:
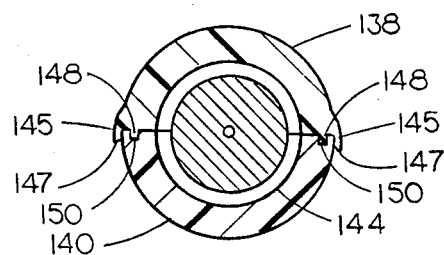
FIG. 13 is a sectional view taken at lines 13—13 in FIG. 12.
Figure 14:
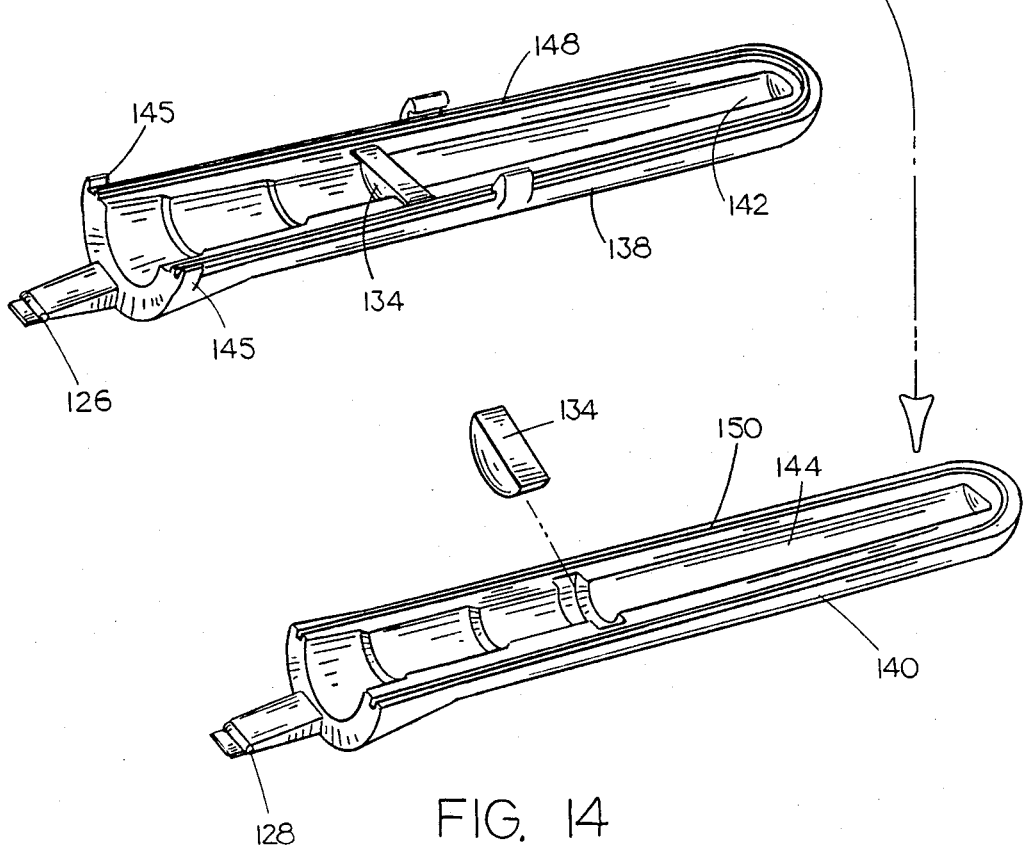
FIG. 14 is an exploded perspective view of the jaws of the invention shown in FIG. 12.

Referring now to FIGS. 12–14, a sixth embodiment of the safety cover of this invention is designated generally at 136 and includes a pair of opposing and cooperable jaws 138 and 140 having longitudinal grooves 142 and 144 therein for encasing a conventional needle 12 upon closure of the jaws. Jaws 138 and 144 are pivotally attached to a syringe barrel 146 having conventional dimensions at hinges 126' and 128'. Safety cover 136 includes a resilient disc-shaped two-piece gasket 134' located and oriented similarly to that of the embodiment of FIGS. 10 and 11. In order to form a seal completely around needle 12, a projecting rib 148 is formed on jaw 138 which corresponds with a groove 150 cut into jaw 140. Rib 148 and groove 150 are each formed on the flat "rim" surface 152 which surrounds grooves 142 and 144 respectively on jaws 138 and 140. As shown in FIG. 13, rib 148 and groove 150 cooperate to form a seal along the periphery of jaws 138 and 140. Gasket 134' serves to seal fluids within the grooves 142 and 144 when a contaminated needle is encased therein.

A pair of guide teeth 145 are provided on jaw member 138 which serve to guide jaws 138 and 140 together in accurate alignment so that rib 148 is aligned with groove 150. Guide teeth 145 have a bevelled edge 147 positioned outward of the width of jaw 140, as seen in FIG. 13. Similar teeth may also be used along the length of jaws 138 and 140 to assist in alignment.

Figure 15:
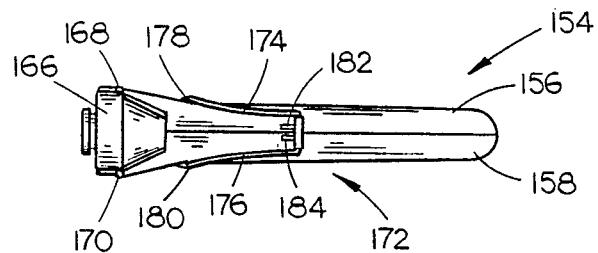
FIG. 15 is a side elevational view of a seventh embodiment of the present invention, with the safety cover closed around a needle.
Figure 16:
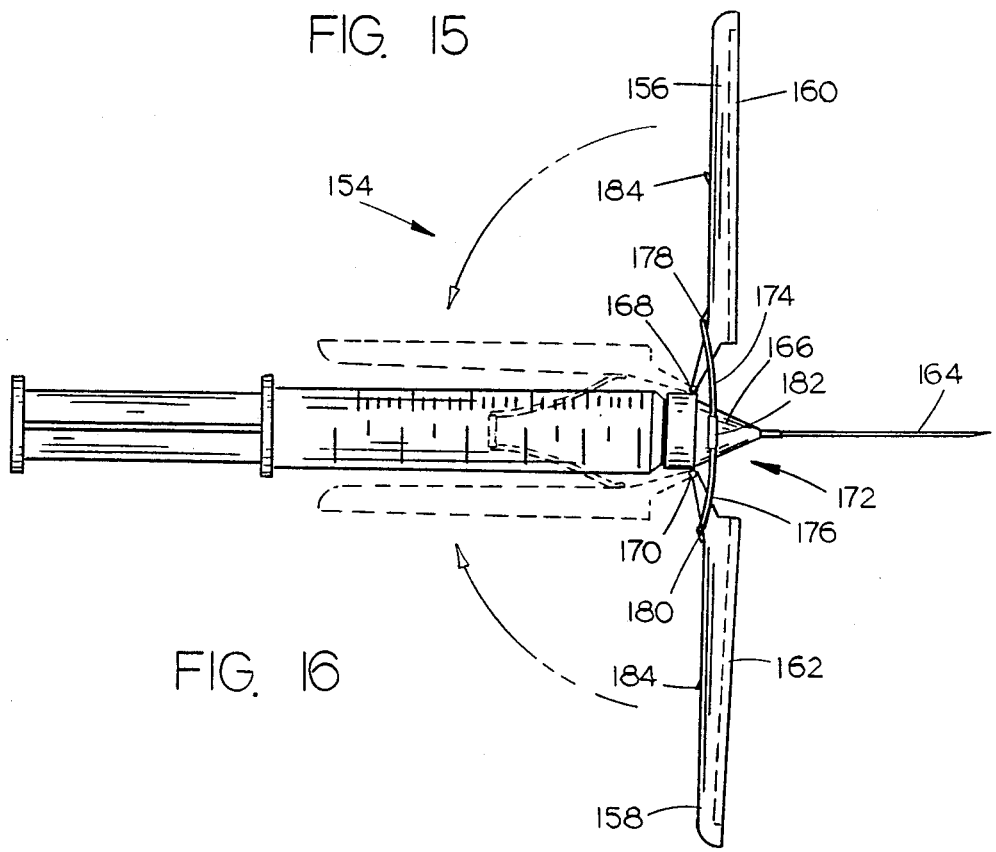
FIG. 16 is a side elevational view of the embodiment shown in FIG. 15 installed upon a syringe and with the jaws partially opened.
Figure 17:
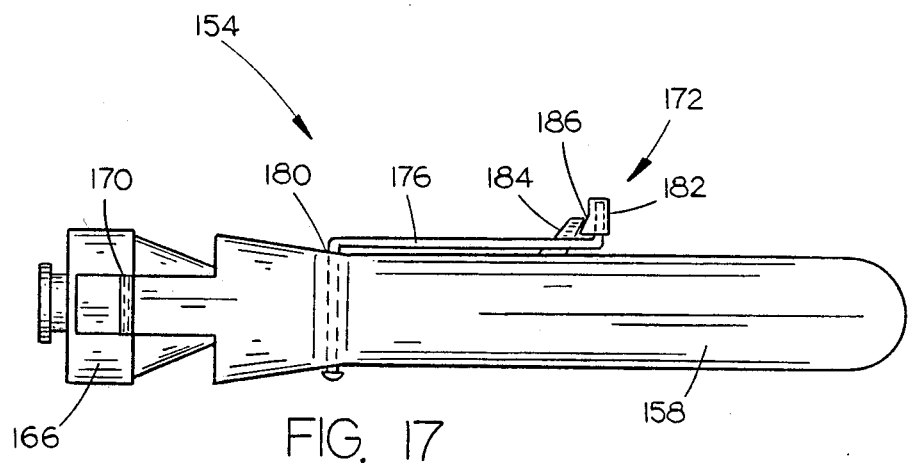
FIG. 17 is a top elevational view of the embodiment of FIG. 15 with the jaws of the safety cover locked in a closed position.

Referring now to FIGS. 15-17 a seventh embodiment of the safety cover of this invention is designated generally at 154 and includes a pair of opposingly disposed semi-cylindrical jaws 156 and 158, each jaw having a longitudinally-oriented groove and 160 and 162, respectively, cut therein to encase a needle 164 therebetween. Jaws 156 and 158 are pivotally connected to a base 166 by hinges 168 and 170, of the type described hereinabove. Base 166 is adapted for connection to a conventional syringe barrel 10 in a conventional manner. Safety cover 154 includes a manually operated actuator designated generally at 172 which will mechanically cause jaws 156 and 158 to open or close.

Mechanical actuator 172 includes a pair of pivotable lever arms 174 and 176, each extending from a pivotal connection 178 and 180 from jaws 156 and 158. A thumb-actuated bar 182 is pivotally connected at each end to lever arms 174 and 176 as shown in the drawings.

In operation, movement of bar 182 along the longitudinal axis of syringe 10 and needle 164 will cause jaws 156 and 158 to pivot on hinges 168 and 170 between an open and closed position. FIG. 16 shows jaws 156 and 158 in a partially open position, and in broken lines, shows jaws 156 and 158 in a completely open position.

A pair of projecting hook members 184 are provided on jaws 156 and 158 to secure bar 182 and retain jaws 156 and 158 in a closed position. Hook members 184 project outwardly a distance to abut a slanted surface 186 on the underside of bar member 182. Slanted surface 186, in conjunction with hook members 184, will cause a positive retention of bar 182 in position. Lever arms 174 and 176 are slightly resilient such that bar 182 may be pulled outwardly away from jaws 156 and 158 to bypass hook members 184 and release bar 182 to open jaws 156 and 158. Lever arms 174 and 176 are slightly arcuate, as shown in the drawings, such that actuator bar 182 is resiliently biased into positive contact with hook members 184. Similarly, to release actuator bar 182 from hook members 184 longitudinal pressure may be applied to slightly straighten lever arms 174 and 176 to increase their length and allow actuator bar 182 to bypass hook members 184.

It can be seen that the hinge mechanism 172 of safety cover 154 allows jaws 156 and 158 to be opened and closed around needle 164 using only one hand. This significantly improves the desirability and efficiency of the safety cover. Although jaw members 156 and 158 are shown attached to base 166 on needle 164, it should be understood that the jaw members could just as easily be mounted on the syringe barrel or on the adaptor in the same manner as described hereinabove in the other embodiments.

Figure 18:
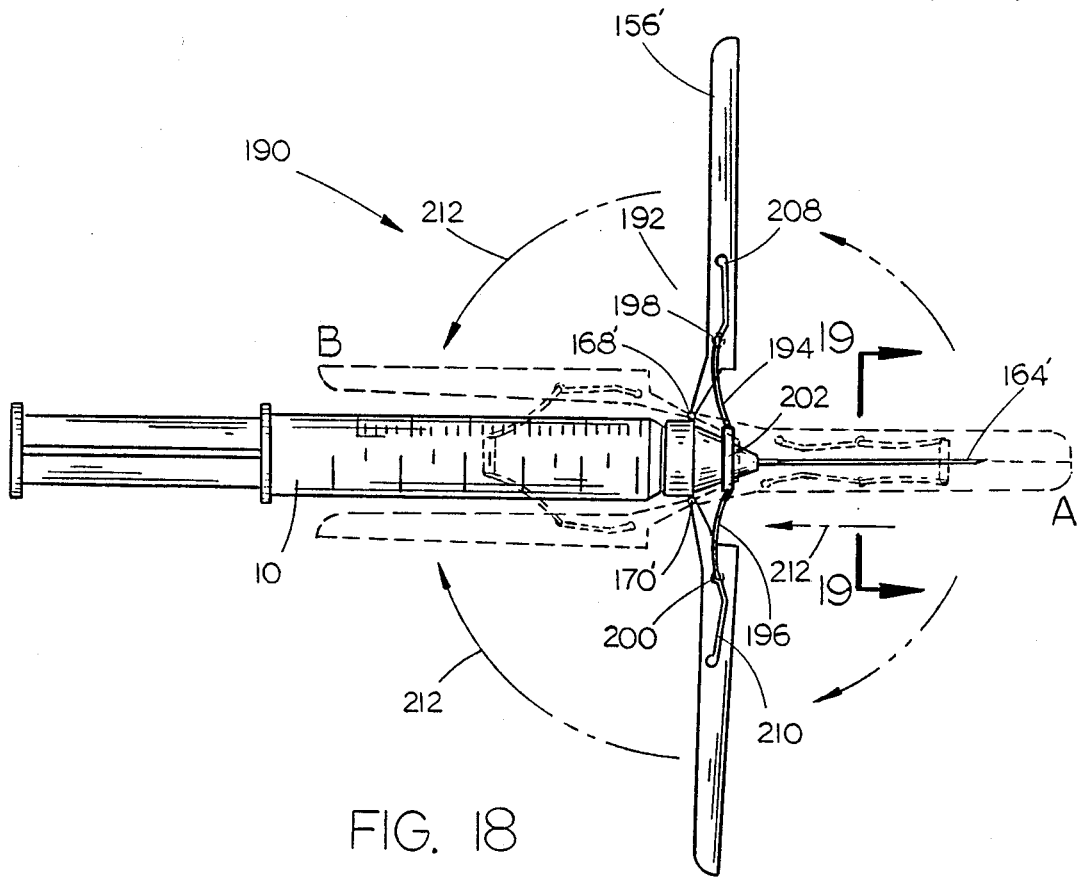
FIG. 18 is a side elevational view of an eighth embodiment of the invention, with the safety cover shown in two different positions in broken lines.
Figure 19:
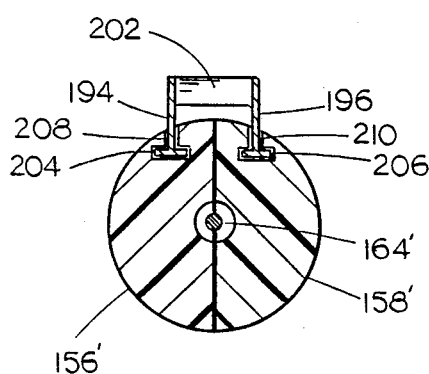
FIG. 19 is a sectional view taken at lines 19—19 in FIG. 18.
Figure 20:
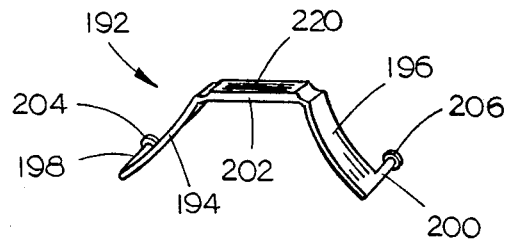
FIG. 20 is an enlarged perspective view of the actuator mechanism of FIG. 18.

FIGS. 18-20 disclose an eighth embodiment of the invention, which is designated generally at 190 and differs from the embodiment of FIG. 16 in the use of a different actuator mechanism 192. Safety cover 190 includes a pair of jaws 156' and 158' pivotally mounted to base 166' which is removably connected to syringe 10. Actuator mechanism 192 includes a pair of lever arms 194 and 196 which are pivotally and slideably connected to jaws 156' and 158' at their ends 198 and 200, respectively. Lever arms 194 and 196 are pivotally connected at their other end to actuator bar 202. Similar to the embodiment of FIGS. 15-17, the actuator bar may be releaseably connected to hook members (not shown) on jaws 156' and 158'. Lever arms 194 and 196 are slightly arcuate, similar to those shown in FIG. 16.

In operation, actuator mechanism 192 begins in position A, shown in broken lines in FIG. 8, with jaws 156' and 158' in a closed position encasing needle 164'. Using the thumb, actuator bar 202 is pushed longitudinally, as shown by arrow 212 to pivot jaws 156' and 158' to a position shown in solid lines in FIG. 18. In this position, foot portions 204 and 206 have moved from one end of slots 208 and 210, to the other end. Continued movement of actuator bar 212 continues to pivot jaws 156' and 158', as shown by arrows 214 to the broken line position B of FIG. 18. Foot portions 204 and 206 slide back to the opposite ends of 208 and 210, thereby holding jaws 156' and 158' in place until pressure on actuator bar 202 is applied in the opposite direction.

FIG. 20 shows an enlarged view of actuator mechanism 192 as used in the embodiment in FIGS. 18 and 19. The inventor has found that mechanism 192 may be a single piece of plastic material which has a pair of scores or scallops 216 and 218 to form the pivotal connection between lever arms 194, 196 and actuator 202. The top surface 220 of actuator bar 202 may be knurled so as to increase frictional grip on bar 202 with the thumb. This same construction of a single-piece actuator bar and lever arms may also be utilized in place of the actuator bar 182 and lever arms 174 and 176 of FIGS. 15-17.

It is therefore believed that the above-described invention fulfills at least all of the above-stated objectives.

I claim:

1. For use with a convention syringe having a male connecting portion thereon for connection to the female connecting portion of a conventional needle, a safety cover, comprising:

a base having female connecting means thereon for removable connection to said male connecting portion of said syringe;

a needle mounted on said base;

a pair of jaw members pivotally mounted on diametric sides of said base to move between a closed position, wherein said jaws are longitudinally abutting, and an open position, wherein said jaws are disposed generally parallel to each other on diametric sides of base;

means on said jaws for selectively, releasably locking said jaws in said closed position; and said jaws having a longitudinal groove therein adapted to form a selectively lockable tubular aperture between said jaws to encase said needle when said jaws are in the closed position.

2. The safety cover of claim 1, wherein said needle is of a length, when taken in combination with said base, substantially equal to that of a conventional needle measured from the female connecting portion to the tip of said conventional needle.

3. The safety cover of claim 1, further comprising actuator means connecting said jaws, for moving said jaws between said open and closed positions.

4. In combination,
a hollow, tubular syringe;
a needle projecting from one end of said syringe;
at least two jaw members operatively, pivotally connected to said syringe, said jaw members being pivotally movable between a closed position, wherein said jaws are longitudinally abutting, and an open position, wherein said jaws are disposed along said syringe; and
said jaw members encasing said needle when said jaws are in said closed position.

5. The combination of claim 4, wherein said jaw members include means for selectively locking and unlocking said jaws in said closed position, whereby said jaws may be selectively unlocked for movement from said closed position to said open position.

6. The safety cover of claim 25, wherein said actuator means includes a handle portion adapted to be gripped and moved to operate said jaws between said open and closed positions.

7. The safety cover of claim 3, wherein said means for selectively releasably locking said jaws in said closed position includes means for releasably holding said actuator means in a fixed position.

8. The safety cover of claim 3, wherein said actuator means includes means for selectively holding said jaws in said open position.

* * * * *